(12) United States Patent
Pedrazzini

(10) Patent No.: US 9,387,989 B2
(45) Date of Patent: Jul. 12, 2016

(54) LABORATORY AUTOMATION SYSTEM WITH COATING TAPE INTERPOSED BETWEEN AN AUTOMATIC CONVEYOR BELT AND A SLIDING PROFILE, AND A METHOD OF APPLYING SAID COATING TAPE

(71) Applicant: Inpeco Holding Ltd., Qormi (MT)

(72) Inventor: Gianandrea Pedrazzini, Paradiso (CH)

(73) Assignee: INPECO HOLDING LTD., Qormi, (MT)

( * ) Notice: Subject to any disclaimer, the term of this patent is extended or adjusted under 35 U.S.C. 154(b) by 0 days.

(21) Appl. No.: 14/995,899

(22) Filed: Jan. 14, 2016

(65) Prior Publication Data
US 2016/0130090 A1   May 12, 2016

Related U.S. Application Data

(63) Continuation of application No. 14/403,444, filed as application No. PCT/EP2013/060535 on May 22, 2013, now abandoned.

(30) Foreign Application Priority Data

May 24, 2012 (IT) .............................. MI2012A0901

(51) Int. Cl.
| | | |
|---|---|---|
| B65G 15/62 | (2006.01) | |
| G01N 35/04 | (2006.01) | |
| B32B 37/14 | (2006.01) | |
| B65G 15/30 | (2006.01) | |
| B65G 15/28 | (2006.01) | |
| B65G 45/00 | (2006.01) | |
| B32B 38/10 | (2006.01) | |

(52) U.S. Cl.
CPC .............. *B65G 15/62* (2013.01); *B32B 37/144* (2013.01); *B32B 38/10* (2013.01); *B65G 15/28* (2013.01); *B65G 15/30* (2013.01); *B65G 45/00* (2013.01); *G01N 2035/0484* (2013.01)

(58) Field of Classification Search
CPC ........ B65G 15/62; B65G 15/30; B65G 15/28; B32B 38/10; B32B 37/14; G01N 35/04; G01N 2035/046; G01N 2035/0484
USPC .................................. 198/841; 422/63, 65, 66
See application file for complete search history.

(56) References Cited

U.S. PATENT DOCUMENTS

| | | | |
|---|---|---|---|
| 2,815,252 A | 12/1957 | Baker | |
| 3,788,455 A | 1/1974 | Dieckmann, Jr. | |
| 5,186,314 A * | 2/1993 | Clopton ................ | B65G 21/06 198/841 |
| 5,314,662 A | 5/1994 | Hemzy et al. | |
| 6,024,204 A * | 2/2000 | van Dyke, Jr. ......... | G01N 35/04 198/379 |
| 6,202,829 B1 | 3/2001 | Van Dyke, Jr. et al. | |
| 6,427,830 B1 | 8/2002 | Ciccorilli | |
| 6,848,572 B1 | 2/2005 | Sisson, Jr. et al. | |

FOREIGN PATENT DOCUMENTS

| | | |
|---|---|---|
| EP | 2225567 A1 | 9/2010 |
| JP | 2003-312823 A | 11/2003 |

\* cited by examiner

*Primary Examiner* — Mark A Deuble
(74) *Attorney, Agent, or Firm* — Jacobson Holman, PLLC.

(57) ABSTRACT

A laboratory automation system is described, comprising an automatic conveyor belt sliding within a sliding profile of a lane, and a coating tape interposed between the automatic conveyor belt and the sliding profile. The sliding profile includes a first region onto which a coating tape is applied by gluing and a second region where a coating tape is attached to a first end by means of a spring and to a second end by means of clamps.

6 Claims, 4 Drawing Sheets

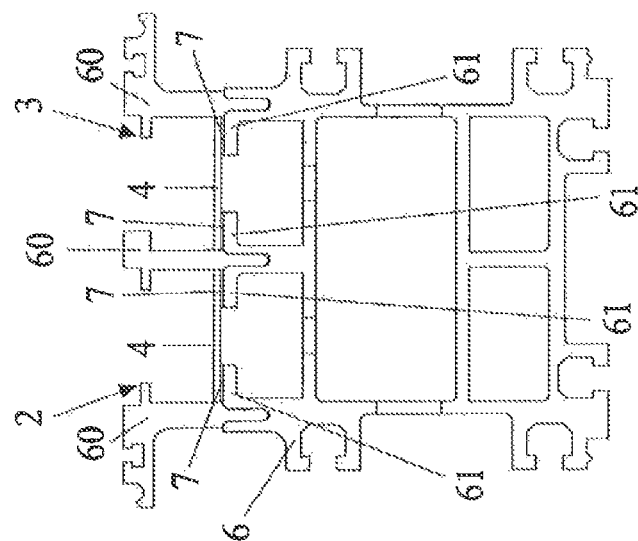
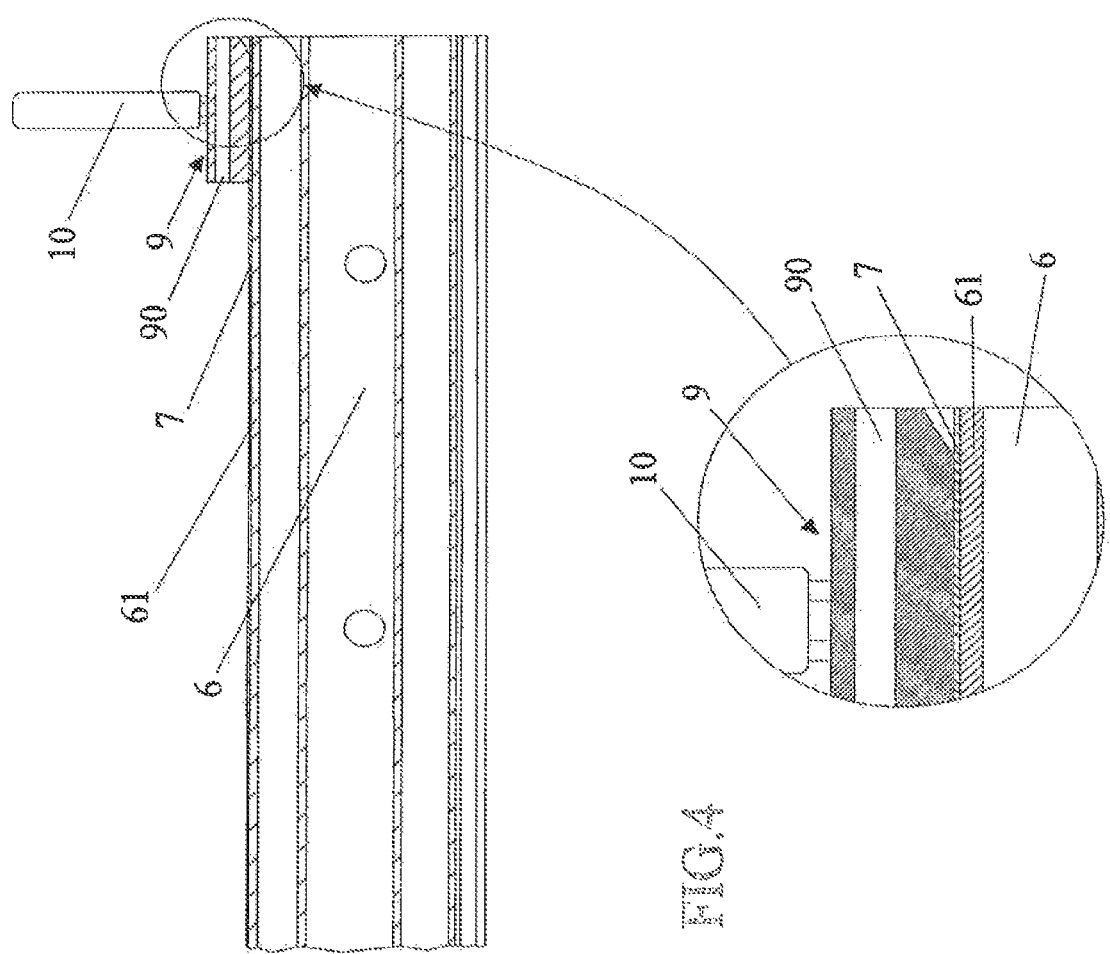

LABORATORY AUTOMATION SYSTEM WITH COATING TAPE INTERPOSED BETWEEN AN AUTOMATIC CONVEYOR BELT AND A SLIDING PROFILE, AND A METHOD OF APPLYING SAID COATING TAPE

The present invention relates to a laboratory automation system with coating tape interposed between an automatic conveyor belt and a sliding profile, and to a method of applying said coating tape.

In laboratories for testing biological material specimens, the use of automated systems for automatically identifying, conveying and directing such specimens towards different points of the laboratory itself is typical.

The system comprises lanes along which the biological product containers travel, each in a transport device (also called "carrier"), on conveyor belts to be suitably directed to the various pre-testing, testing or post-testing modules which interface with the automation system.

The automation system is almost continuously operating during the day, according to the often high operating volumes of a testing laboratory, and it is understood that problems occur with time due to the deposition of dust or dirt in general, related to the use of the belts which, in addition to being damaging from the aesthetic point of view, may in some cases impair the functionality of some mechanical or electronic components arranged along the automation system, besides preventing a smooth sliding of the belts and of the transport devices on the belts.

Moreover, the continuous use of the automation system generally subjects the motors which drive the belts themselves to a considerable strain, due to the friction that is generated in the contact between belts and profile, typically made of aluminum, of the automation system.

U.S. Pat. No. 6,427,830 and JP2003312823 describe conveyor belts for automatic laboratory systems.

The object of the present invention is to provide an automation system with conveyor belts along lanes, in which the sedimentation of dust or dirt of any type along the system is prevented and which simultaneously ensures a smoother sliding of the belts compared to the known solutions, by decreasing the friction between the conveyor belts and the aluminum profile on which they slide.

A further object of the present invention is to provide an automation system with conveyor belts along lanes, in which the motors that drive the belts are subjected to a lower stress, thus reducing the risk of failure and/or breakage.

In accordance with the invention, this and other objects are achieved by an automation system as described in claim 1.

Yet another object of the present invention is to provide a method of applying a coating tape interposed between an automatic conveyor belt and a sliding profile in an automatic laboratory system.

In accordance with the invention, said further object is achieved by a method of applying an adhesive coating tape interposed between an automatic conveyor belt and a sliding profile in a laboratory automation system, characterized in that it comprises applying the adhesive coating tape onto a region of the sliding profile by means of application means which are longitudinally slid over said adhesive coating tape over the whole length of said region without ever being lifted until the opposite end of the region is reached, and while said application means moves forward, a silicone-treated paper film is simultaneously gradually removed from said adhesive coating tape which is gradually glued to the region.

These and other features of the present invention will become more apparent from the following detailed description of an embodiment thereof, shown by way of non-limiting example with reference to the accompanying drawings, in which:

FIG. 1 shows a perspective view of a portion of the automation system;

FIG. 2 again shows a perspective view of a portion of the system, including the elements required for carrying out the first application step;

FIG. 4 shows a sectional view according to line IV-IV in FIG. 3, with an enlarged portion;

FIG. 5 shows a view similar to that in FIG. 3, once the first application step has been completed;

Figure 1:
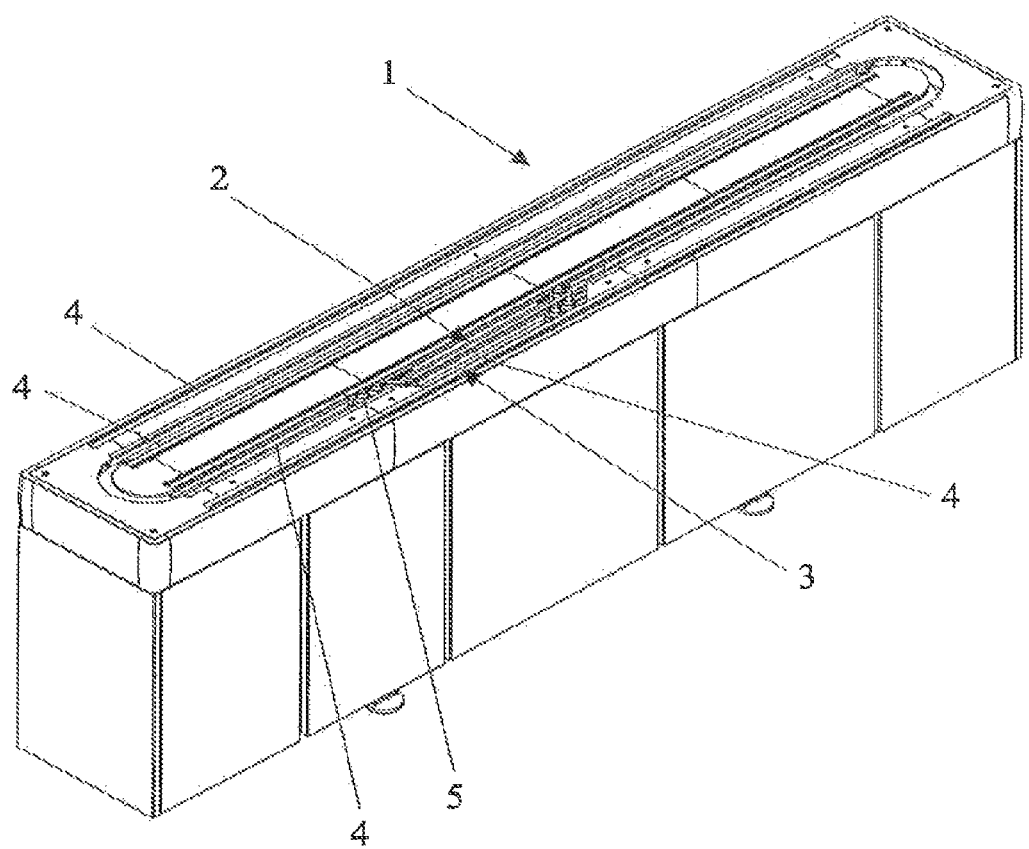

A laboratory automation system comprises primary lanes 2 and secondary lanes 3 parallel to one another, which accommodate parallel motor-driven conveyor belts 4 made of polyurethane, having the function of carrying tube transport devices 5.

The transport devices 5 are usually diverted to the secondary lane 3 for allowing them to reach or go over pre-testing, testing or post-testing modules or stations.

The system consists of modules 1 (FIG. 1) assembled to one another in a variable number and according to different configurations for meeting the different requirements of testing laboratories.

A pair of belts 4 sliding in one direction and a pair of belts 4 sliding in the opposite direction (FIG. 1) are provided for each rectilinear stretch of the system (angle and T-joints are further provided, as will be described hereafter).

Figure 3:
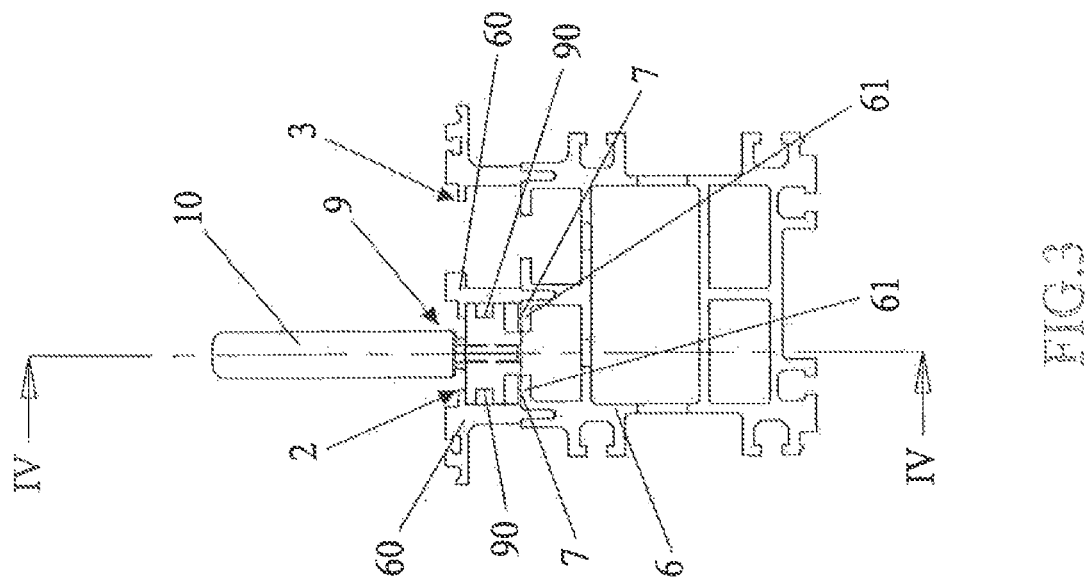
FIG. 3 shows a front view of the view shown in FIG. 2.
Figure 2:
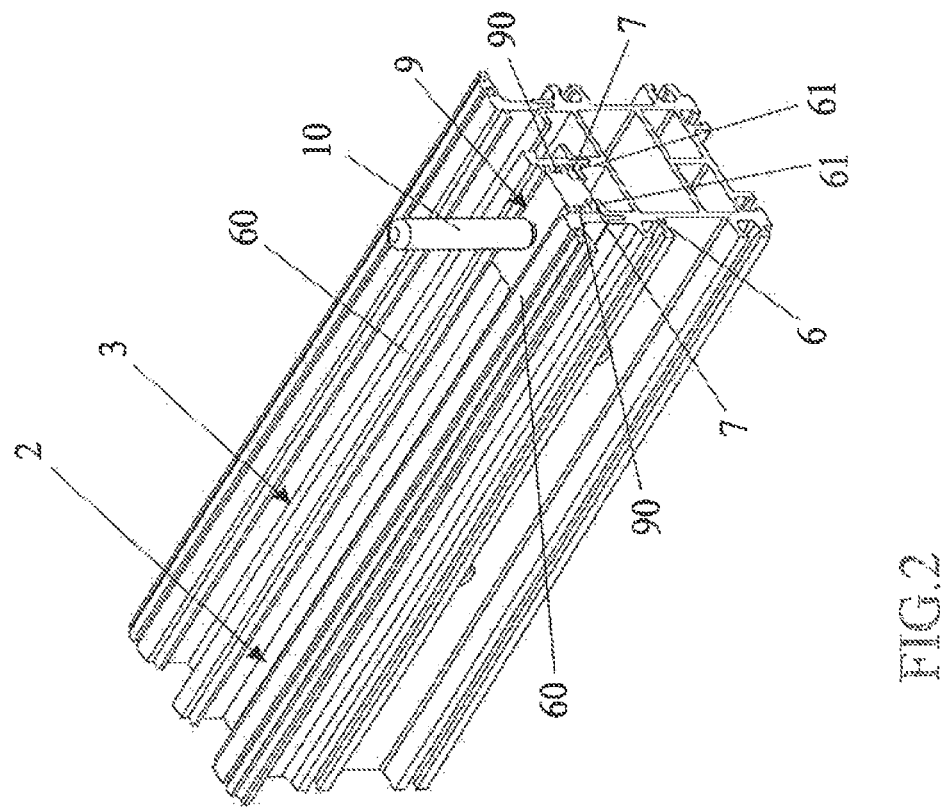

Each pair of lanes 2, 3 is obtained from a sliding profile 6 of belt 4, suitably shaped and advantageously made of aluminum (FIGS. 2 and 3, where profile 6 is shown with reference to a single pair of lanes).

Each belt 4 is made of cell-like polyurethane coated with impregnated fabric which ensures a low friction coefficient with the resting surface of the transport device 5 while moving.

Figure 6:
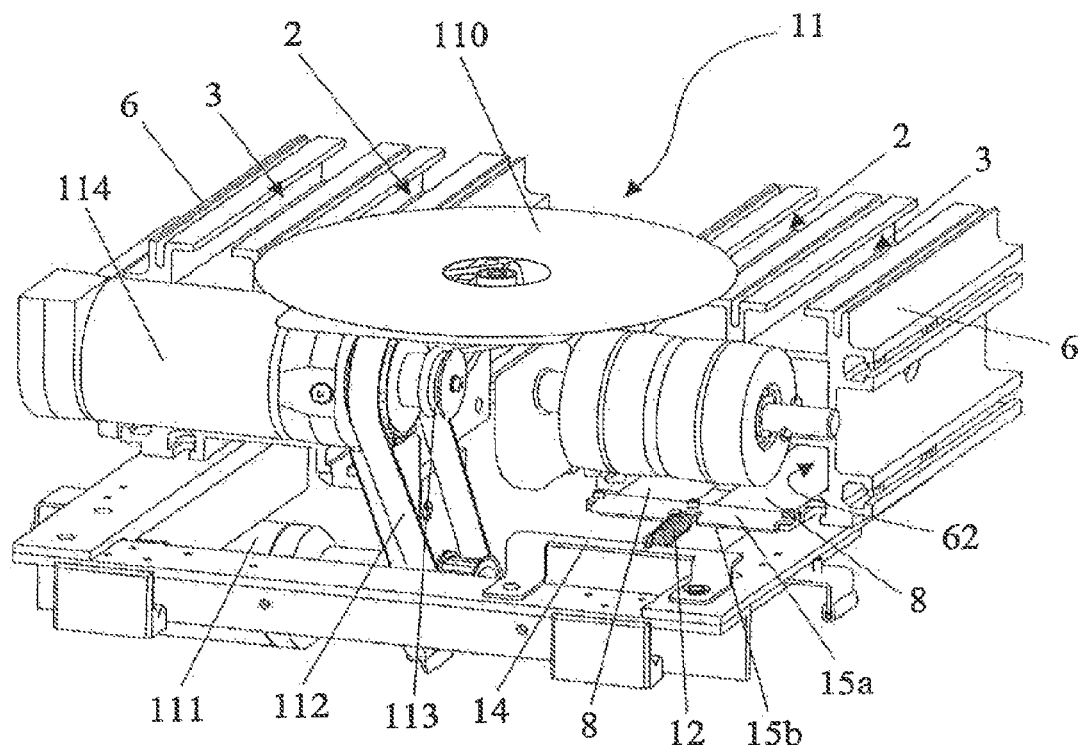
FIG. 6 shows a perspective view of a first end of the system, including the elements required for carrying out the second application step.

A motion inversion device 11 (FIG. 6) is arranged at each end of the transport system in order to allow the transport device 5 to reverse the motion direction, which motion inversion device has the function of transferring each transport device 5 moving from the pair of belts 4 sliding in one direction to the pair of belts 4 sliding in the opposite direction. Said motion inversion device 11 comprises a thin plastic disc 110 driven by a motor 111 which is present at each end of the transport device and which, in addition to generating the rotation of disc 110, also has the function of moving one of the two pairs of belts 4. In fact, the movement is transmitted by means of a first belt 112 and a second belt 113 to a pulley 114 which, by rotating, generates the movement of the pair of belts 4.

Figure 7:
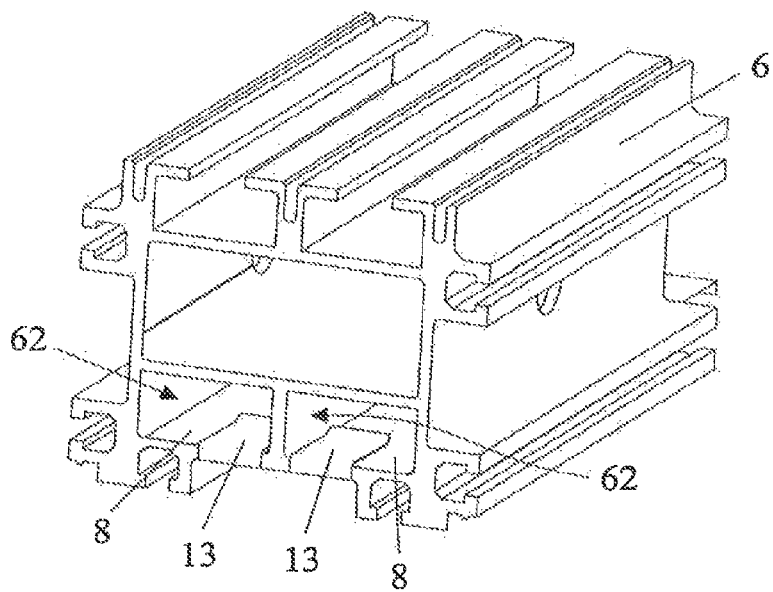
FIG. 7 shows a perspective view of a second end of the system without motor-driven means.

Therefore, each pair of conveyor belts 4 has a rotational motion about pulleys 114 which support it at the ends. In FIG. 7, belts 4 have been removed for convenience.

When the transport device reaches the end of belt 4, the rotational motion of disc 110 allows the transport device 5 to move to belt 4 in the opposite direction, in turn driven by the respective pulley (not shown in FIG. 6) at the other end of the system portion.

As mentioned, the transport system is a modular structure comprising a variable number of transport modules 1. This feature allows the transport system to be adapted to the different testing laboratories where it is installed, meeting the logistical requirements (in terms of space and/or number of analyzers) of any laboratory. Such an object is also achieved by using angular L-shaped modules, where the trajectory of the automation system bends by 90°, or of T-shaped turning modules which serve as side branches of the system. For a detailed description thereof, as well as for other structural details of a known laboratory automation system, reference will be made to patent EP-2225567 already filed by the Applicant.

The method of the present invention consists in applying a thin coating tape 7, 8 made of stainless steel (having a thickness of about one tenth of millimeter) for each lane 2, 3 which coating tape is interposed between the sliding profile 6 and the conveyor belts 4, so that, in contact with the belts themselves, it favors a smoother sliding thereof compared to the known solutions, while considerably reducing the formation of dust and dirt related to the continuous use of the system.

In particular, as regards the part of belts 4 that is visible along the automation system, the application is obtained by pressing, by means of a special tool 9 provided with a handle 10, two strips 7 of such a stainless steel coating tape at the side ends of each lane 2, 3, i.e. along a first region 61 of the sliding profile 6 (FIGS. 2, 3 and 4).

In any case, such strips 7 do not exceed the width of region 61 (FIGS. 2 and 3) and are adhesive on the contact side with such a region, so that the pressure exerted with tool 9 thereon favors its gluing to profile 6; likewise, as is obvious, strips 7 must cover the whole length of the region 61 of profile 6 (FIG. 4, where the upper profile 60 of profile 6 has been removed for favoring the full view of a section of tool 9).

It should be noted that the application of such strips 7 one at a time takes place without interruption; in fact, once such an operation has begun, tool 9 is longitudinally slid over the whole first region 61 and is never lifted, until the opposite end of region 61 itself is reached. At the same time, while tool 9 moves forward, the silicone-treated paper film is gradually removed from the adhesive strip 7, which is then gradually glued along region 61.

Moreover, as is apparent from FIGS. 2 and 3, tool 9 cannot even lift during such an operation because, being inserted from the side of profile 6, it is then vertically locked by the presence of the upper profile 60.

Moreover, this meets the precise requirement of applying the adhesive strip 7 on system portions already assembled, without the need of removing the upper profile 60.

To this end, it should be noted that recesses 90 (FIGS. 2 and 3) of tool 9 allow the impact of tool 9 with any stopping gates, laterally protruding from lanes 2, 3 towards their interior, to be prevented when applying strip 7.

At the end of the application of strips 7, when the polyurethane conveyor belts 4 are then laid along lanes 2, 3, strips 7 are interposed between belts 4 and profile 6 (FIG. 5).

As regards the part of belts 4 which, when wound again about pulley 114, is inserted in a second region 62 of profile 6 (i.e. in a non-visible part of the system), lightly touching the top wall thereof, a third strip 8 (FIGS. 6-7) of the stainless steel coating tape, which is much wider than the previous two but has the same thickness of about one tenth of millimeter, is applied for each lane 2, 3.

It also travels the whole length of the rectilinear stretch of the system and is attached to the ends on one side by means of a spring 12 (FIG. 6) and on the other side by means of clamps 13 (FIG. 7, where the part of profile 6 hidden from view by pulley 114 is shown).

The choice about which of the two ends in length of profile 6 should be used for fixing by means of spring 12 or clamps 13 may vary according to the cases (rectilinear, L-shaped or T-shaped module) and according to different design choices.

In the first case, spring 12 is coupled on one side to a bracket 14 and on the other side to a pair of flanges 15a, 15b screwed to each other and trapping the steel strips 8 of a pair of lanes 2, 3 which protrude from the bottom wall of the second region 62.

In the second case, the steel strips 8 are instead directly clamped to the bottom wall of region 62 by means of clamps 13.

Each steel strip 8 is not adhesive, unlike the two strips 7 described above, and exerts a cleaning action on belt 4 in the central sliding part thereof along a rectilinear stretch of the system; in fact, in such a sliding region hidden from view, the tension that belt 4 has in the surface part is missing, and thus belt 4 rubs against the steel strip 8, thus being cleaned.

It is again noted that belts 4 are not shown in FIG. 7 since a depiction thereof would hinder the view of strips 8.

The innovative aspect of the invention is therefore given by the application of coating tapes 7, 8 made of stainless steel, aimed to contact the polyurethane belts 4 which move the transport devices 5 along the automation system; the application of such tapes 7, 8 is intended to decrease the friction caused, in the known solutions, by the sliding movements of belts 4 directly in contact with the aluminum profile 6.

The decrease in the friction reduces the strain exerted by the motors driving the conveyor belts 4, and accordingly, it is more unlikely that the motor themselves show wear problems due to their operation day after day.

Moreover, as previously mentioned, the application of the coating tapes 7, 8 is intended to carry out a cleaning action on the conveyor belts 4, considerably reducing the sedimentation of dust and dirt along the automation system, also related to the continuous use of the system itself.

Several changes and variations may be made to the invention thus conceived, all falling within the scope of the inventive concept.

In the practice, the materials used as well as shapes and sizes, may be any, according to the requirements.

The invention claimed is:

1. A laboratory automation system comprising an automatic conveyor belt sliding within a sliding profile of a lane, and a coating tape interposed between the automatic conveyor belt and the sliding profile, characterized in that said sliding profile includes a first region onto which a coating tape is applied by gluing and a second region where a coating tape is attached to a first end of said second region by means of a spring and to a second end of said second region by means of clamps.

2. A system according to claim 1, wherein the spring is coupled on one side to a bracket and on the other side to a pair of flanges screwed to each other and supporting the coating tape.

3. A system according to claim 1, wherein the sliding profile comprises primary lanes and secondary lanes parallel to one another and the automatic conveyor belt comprises a pair of parallel motor-driven conveyor belts each of which is accommodated in a respective lane, said coating tape of said first region comprising a first strip and a second strip each of which is interposed between the sliding profile and the conveyor belts of a respective lane.

4. A system according to claim 2, wherein the sliding profile comprises primary lanes and secondary lanes parallel to one another and the automatic conveyor belt comprises a pair of parallel motor-driven conveyor belts each of which is accommodated in a respective lane, said coating tape of said first region comprising a first strip and a second strip each of which is interposed between the sliding profile and the conveyor belts of a respective lane.

5. A system according to claim 3, wherein said coating tape of said second region comprises a third strip which is wider than the first and second strips applied for each lane.

6. A system according to claim 4, wherein said coating tape of said second region comprises a third strip which is wider than the first and second strips applied for each lane.

* * * * *